United States Patent [19]

Shay

[11] Patent Number: 4,707,449

[45] Date of Patent: Nov. 17, 1987

[54] PICHIA PASTORIS YEAST STRAINS OF ENHANCED TRYPTOPHAN CONTENT

[75] Inventor: Lucas K. Shay, Bartlesville, Okla.

[73] Assignee: Phillips Petroleum Company, Bartlesville, Okla.

[21] Appl. No.: 632,499

[22] Filed: Jul. 19, 1984

[51] Int. Cl.$^4$ .......................... C12N 1/16; C12P 21/00
[52] U.S. Cl. ...................................... 435/255; 435/68; 435/108; 435/172.1; 435/247; 435/804; 435/938; 426/60; 426/62
[58] Field of Search ...................... 435/68, 108, 172.1, 435/247, 255, 804, 938; 426/60, 61, 62

[56] References Cited

U.S. PATENT DOCUMENTS

| | | |
|---|---|---|
| 3,385,762 | 5/1968 | Okazaki et al. |
| 3,591,456 | 7/1971 | Tanaka et al. |
| 3,594,279 | 7/1971 | Nakayama et al. |
| 3,700,559 | 10/1972 | Shiio et al. |
| 3,915,796 | 10/1975 | Paulsson et al. ............... 435/108 |
| 4,271,267 | 6/1981 | Yukawa et al. |
| 4,342,835 | 8/1982 | Hitzman et al. ............... 435/804 |
| 4,414,329 | 11/1983 | Wegner. |
| 4,439,525 | 3/1984 | Shay et al. ............... 435/938 |

FOREIGN PATENT DOCUMENTS 1196391  6/1970  United Kingdom ............... 435/255

OTHER PUBLICATIONS

Cooney et al, "Microbial Utilization of Methanol", *Advances in Applied Microbiology*, vol. 15, D. Perlman Ed. (Academic Press 1972), pp. 337–365.
*Process Biochemistry*, May, 1978, p. 1.
Riviere, *Industrial Applications of Microbiology*, (John Wiley & Sons, New York 1977, English Edition), Chapter 4, "Microbial Proteins".
Search Summary on "Tryptophan as Animal Feed".
Umbarger, "Metabolite Analogs as Genetic and Biochemical Probes", *Adv. Genet.* 16, pp. 119–140 (1971).

*Primary Examiner*—Charles F. Warren
*Assistant Examiner*—Irene Marx
*Attorney, Agent, or Firm*—Lyell H. Carver

[57] ABSTRACT

Mutant *Pichia pastoris* yeasts which produce relatively high levels of tryptophan. These high tryptophan capability *Pichia pastoris* mutants, grown on such as methanol or glucose, produce improved amino acid balance single-cell protein product reducing the need to supplement single-cell protein with tryptophan when used as food supplements.

7 Claims, No Drawings

PICHIA PASTORIS YEAST STRAINS OF ENHANCED TRYPTOPHAN CONTENT

FIELD OF THE INVENTION

The invention pertains to novel strains of *Pichia pastoris* yeasts. In another aspect, the invention pertains to *Pichia pastoris* yeast strains with enhanced tryptophan-producing capabilities. In a further aspect, the invention pertains to methods of producing, and the single cell protein products resulting from, culturing the tryptophan-enhanced yeast strains.

BACKGROUND OF THE INVENTION

Yeasts are known for a high nutritional value, and have been used as feed supplements, both for animals, and to some extent for humans. Yeasts have a high protein content in general, and probably contain more B-group vitamins than most other protein sources, $B_{12}$ a notable exception. *Pichia pastoris* strains are becoming known for usefulness as high-productivity strains in single cell protein (SCP) processes, but none have been reported with high tryptophan content.

TABLE I

ESSENTIAL AMINO ACIDS OF SOME PROTEIN SOURCES[a][b]

| Amino Acids | Wheat | Egg White | Spirulina maxima | Saccharomyces cerevisiae | Candida lipolytica (gas oil) | Pseudomonas (methanol) | Alcaligenes eutrophus | Penicillium notatum | Pichia pastoris NRRL Y-11430[c][d] |
|---|---|---|---|---|---|---|---|---|---|
| Lysine | 2.8 | 6.5 | 4.6 | 7.7 | 7.8 | 5.3 | 8.6 | 3.9 | — |
| Threonine | 2.9 | 5.1 | 4.6 | 4.8 | 5.4 | 4.5 | 4.5 | — | — |
| Methionine | 1.5 | 3.2 | 1.4 | 1.7 | 1.6 | 1.8 | 2.7 | 1 | — |
| Cystine | 2.5 | 2.4 | 0.4 | — | 0.9 | 0.3 | — | — | — |
| Tryptophan | 1.1 | 1.6 | 1.4 | 1.0 | 1.3 | — | 1.1 | 1.25 | 1.1 |
| Isoleucine | 3.3 | 6.7 | 6.0 | 4.6 | 5.3 | 3.9 | 4.6 | 3.2 | — |
| Leucine | 6.7 | 8.9 | 8.0 | 7.0 | 7.8 | 7.0 | 8.5 | 5.5 | — |
| Valine | 4.4 | 7.3 | 6.5 | 5.3 | 5.8 | 5.9 | 7.1 | 3.9 | — |
| Phenylalanine | 4.5 | 5.8 | 5.0 | 4.1 | 4.8 | 4.2 | 4.0 | 2.8 | — |

[a]Data from p. 110 Industrial Applications of Microbiology, J. Riviere (Wiley 1977), except for P.p. NRRL Y-11430.
[b]The values shown are g amino acid/100 g protein.
[c]Tryptophan amino acid analysis of NRRL Y-11430 made by colorimetric methods.
[d]Tryptophan content in *Pichia pastoris* Y-11430 is 1.1 g/100 g protein (as shown), which equals 0.67 g/100 g weight cells, grown on glucose substrate.

TABLE II

| Essential Amino Acid composition of Various Food Yeasts[a][b] | | | | |
|---|---|---|---|---|
| Amino Acid | S. cerevisiae molasses | Candida utilis sulphite liquor | S. fragilis milk whey | S. cerevisiae beer |
| Lysine | 8.2 | 6.7 | 8.8 | 7.3 |
| Valine | 5.5 | 6.3 | 6.6 | 5.2 |
| Leucine | 7.9 | 7.0 | 9.9 | 6.3 |
| Isoleucine | 5.5 | 5.3 | 5.5 | 5.7 |
| Threonine | 4.8 | 5.5 | 5.5 | 4.8 |
| Methionine | 2.5 | 1.2 | 1.5 | 1.2 |
| Phenylalanine | 4.5 | 4.3 | 3.9 | 4.4 |
| Tryptophan | 1.2 | 1.2 | 1.5 | 1.1 |
| Histidine | 4.0 | 1.9 | 2.5 | 1.5 |
| Arginine | 5.0 | 5.4 | 4.9 | 4.7 |

[a]Data from p. 110 Industrial Applications of Microbiology, J. Riviere, (Wiley 1977), except for P.p. NRRL Y-11430.
[b]The values shown are g amino acid/100 g protein.

As can be seen above, tryptophan content generally is relatively low in yeasts. Needed are *Pichia pastoris* yeasts that have good productivity in single cell protein production, but with much increased (enhanced) tryptophan content.

BRIEF DESCRIPTION OF THE INVENTION

I have caused the formation of and thus have invented several viable stably reproducible strains of mutant yeasts of *Pichia pastoris* which strains result in single cells whose protein contains much increased amounts of tryptophan, up to some 2.8× the group parent tryptophan content. These mutant high tryptophan strains are employable in the production of single cell protein (SCP). The so-produced single cell protein product utilizing these mutant high-tryptophan yeasts has much improved tryptophan content to the extent that supplementation for feed use purposes with added tryptophan can be greatly reduced or indeed even eliminated.

My invention includes in its several aspects six new and novel *Pichia pastoris* mutant yeast strains of desirably increased tryptophan content, which strains have been deposited prior to the filing of this application with the United States Department of Agriculture, Northern Regional Research Laboratory and received individual depository numbers as hereinafter disclosed, mutants thereof which are strains derived from any thereof and also exhibit high tryptophan-producing capabilities, and successive generations of any of these.

It is an object of my invention to provide *Pichia pastoris* yeast strains exhibiting enhanced tryptophan-producing capabilities. It is a further object of my invention to provide a process of fermentation to culture these unique *Pichia pastoris* mutants. An additional object of my invention is the protein product resulting from the culturing of these strains or their progeny.

DETAILED DESCRIPTION OF THE INVENTION

To the best of my knowledge, no *Pichia pastoris*-derived strains of increased tryptophan-producing capability have heretofore been developed.

Improved Tryptophan Containing *Pichia Pastoris* Strains Base Strain

My six novel mutant *Pichia pastoris* strains of improved tryptophan content are novel off-spring (mutants) of *Pichia pastoris* NRRL Y-12451. *Pichia pastoris* NRRL Y-12451 itself is disclosed and claimed in U.S. Pat. No. 4,439,525 (Shay and Wegner, Mar. 27, 1984) as a strain of enhanced methionine capability. *Pichia pastoris* NRRL Y-12451 itself is an offspring mutant strain of *Pichia pastoris* NRRL Y-11430, the latter a strain disclosed in and its use claimed in U.S. Pat. No. 4,414,329 (Wegner, Nov. 8, 1983).

The grandparent strain *Pichia pastoris* NRRL Y-11430 and the parent mutant strain NRRL Y-12451 each were duly deposited with the United States Department of Agriculture, Agricultural Research Service, Northern Regional Research Laboratory, Peoria, Ill. 61604, as disclosed in U.S. Pat. No. 4,414,329 and U.S. Pat. No. 4,439,525.

In accordance with one aspect of my invention, I have developed six new, unique, novel, and useful mutant *Pichia pastoris* strains from *Pichia pastoris* NRRL Y-12451. My six mutant *Pichia pastoris* strains each exhibit highly enhanced tryptophan producing capabilities. I further consider as my invention strains or mutants thereof, or strains derived from any thereof and which also exhibit high tryptophan-producing capabilities, and successive generations of any of these or of such.

Prior to filing this application, I have deposited appropriate samples of each of my six novel *Pichia pastoris* yeast strain cultures with the United States Department of Agriculture, Agricultural Research Service, Northern Regional Research Laboratory, Peoria, Ill. 61604, by depositing therewith two agar/slant cultures of each strain, and have received from the aforesaid depository individual strain designations as follows:

TABLE III

| Culture Name | My Strain Designation | USDA-NRRL Depository Designation |
|---|---|---|
| *Pichia pastoris* | A79 | NRRL Y-15251 |
| *Pichia pastoris* | A150 | NRRL Y-15252 |
| *Pichia pastoris* | F5-133 | NRRL Y-15253 |
| *Pichia pastoris* | F10-76 | NRRL Y-15254 |
| *Pichia pastoris* | F10-211 | NRRL Y-15255 |
| *Pichia pastoris* | H-42 | NRRL Y-15256. |

These unique *Pichia pastoris* cultures have been deposited in accordance with the procedures of the aforesaid depository, and of the United States Patent and Trademark Office, such that these strains will be available during pendency of this patent application to one determined by the Commissioner of Patent and Trademarks to be entitled thereto, as required by Rules of Practice in Patent Cases and 35 U.S.C. 122. The deposits were made in accordance with United States Patent and Trademarks Office practice such that all restrictions on availability to the public of samples of the strains will be removed upon granting of a United States Patent of which these important strains are the subject. Culture samples from these deposits, or from my cultures from which the deposits were made, thus provide ready availability of samples of strains of my discovery.

These novel and unique *Pichia pastoris* microorganism strains have each been classified as follows:

TABLE IV

| Division: | Ascomytina |
|---|---|
| Class: | Hemiascomycetes |
| Order: | Endomycetales |
| Family | Saccharomycetaceae |
| Genus: | Pichia |

The novel and unique strains of microorganisms can be further characterized by properties as shown in the following tabulation:

TABLE V[a]

| | Characteristic Mutant Isolate | | | | | |
|---|---|---|---|---|---|---|
| | A79 | A150 | F5-133 | F10-76 | F10-211 | H-42 |
| Gram Staining | Yes | → | → | → | → | → |
| Sporulation | Yes | → | → | → | → | → |
| Colony Appearance | All were circular raised | | | | → | → |
| | IM1M Plates | | | | | |
| Plus Biotin | + | + | + | + | + | + |
| No Biotin | ± (faint) | → | → | → | → | |
| Colony Appearance (Plus Biotin) | All were circular raised; white | | | → | → | |
| | IM2 Plates Plus 0.5 Wt/Vol % Glucose | | | | | |
| | + | + | + | + | + | + |
| | IM2 Plates Plus 0.5 Wt/Vol % Sucrose | | | | | |
| | – | – | – | – | – | – |
| | IM2 Plates Plus 0.5 Wt/Vol % Ethanol | | | | | |
| | + | + | + | + | + | + |
| | IM2 Plates Plus 0.5 Wt/Vol % Formaldehyde | | | | | |
| | – | – | – | – | – | – |
| | PC | | | | | |
| | + | + | + | + | + | + |
| | NB Agar | | | | | |
| | + | + | + | + | + | + |

[a] + = positive vigorous growth.
— = no growth noted.
± = faint growth, no vigor.

In one aspect, my invention of these strains is particularly important in that these strains are *Pichia pastoris* alcohol-assimilating strains. This is considered important since not all *Pichia pastoris* strains assimilate a lower alcohol. *Pichia pastoris* strains, at least certain ones, that exhibit high productivity, that can assimilate a relatively cheap and available carbon energy substrate, such as methanol or glucose, and be useful in a high cell density process such as described and claimed in the aforesaid U.S. Pat. No. 4,414,329, and further have enhanced tryptophan capability over other *Pichia pastoris* strains, are highly desirable in the single cell protein (SCP) field of endeavor.

Microorganisms must possess controls over the biosynthesis of their cellular components such as amino acids, including regulatory mechanisms so that they tend not to overproduce unnecessary metabolites. It is generally theorized that two primary mechanisms are involved in the biosynthesis of amino acids by microorganisms: (1) the allosteric inhibition of enzyme activity through feedback inhibition of the first reaction in this productive sequence by the end product of the reactions; and (2) coarse control which may be described as the genetic repression or derepression of enzyme synthesis. I believe it likely that the biosynthesis of tryptophan in yeast strains is governed by both mechanisms.

Since the biosynthesis of tryptophan seemed to me to be tightly controlled by any given strain of yeast cells, it appeared to me that addition or insertion of extra copies of genes coded for the biosynthetic enzymes was unlikely to result in the production of much if any in the way of increased tryptophan.

I have been successful in interfering in the otherwise tightly controlled regulatory mechanisms of the cells to effectuate the production of mutant strains of *Pichia pastoris* which overproduce tryptophan. The method employed appears to have caused the desensitization of the regulatory mechanism governing tryptophan synthesis.

EXAMPLES

Examples provided are intended to assist one skilled in the art to a further understanding of my invention. Particular materials employed should be considered as exemplary and not limitative. The Examples are part of my disclosure. The specification including text, Examples, data, and claims, should be viewed as a whole in considering the reasonable and proper scope of my invention.

In Table V hereinabove, and in the Example provided hereinafter, reference is made to various media. Some media are standard, such as YM, and some are variations of standard media. For convenience, the composition of media referred to herein are shown below in Tables VI and VII:

Unless other wise indicated, ingredients below are per liter of water:

TABLE VI

| YM | |
|---|---|
| yeast extract | 3 g |
| malt extract | 3 g |
| peptone | 5 g |
| dextrose | 10 g |
| agar | 15 g |
| PC-Plate Count Agar | |
| tryptone | 5 g |
| yeast extract | 2.5 g |
| dextrose | 1 g |
| agar | 15 g |
| NB-Nutrient Broth Agar | |
| beef extract | 3 g |
| peptone | 5 g |
| agar | 15 g |

TABLE VII

| Medium Code | Composition[a] | |
|---|---|---|
| IM1 | $KH_2PO_4$ | 5.0 g |
| | $CaCl_2.2H_2O$ | 0.1 g |
| | $MgSO_4.7H_2O$ | 0.5 g |
| | KCl | 0.5 g |
| | $(NH_4)_2SO_4$ | 3.0 g |
| | TM[b] | 2.5 mL |
| | $H_2O$ | 1.0 L |
| IM1M | IM1 + 0.5 vol. % methanol | |
| IM1G | IM1 + 5 g glucose | |
| IM1GA | IM1G + 20 g/L L-abrine | |
| IM1GFT | IM1G + 5 g/L 5-fluoro-L-tryptophan | |
| IM2 | $KH_2PO_4$ | 2.0 g |
| | $K_2HPO_4$ | 3.0 g |
| | $MgSO_4.7H_2O$ | 0.4 g |
| | $CaCl_2.2H_2O$ | 0.04 g |
| | NaCl | 0.1 g |
| | $(NH_4)_2SO_4$ | 2.0 g |
| | TM[b] | 1.0 mL |
| | $H_2O$ | 1.0 L |
| IM2G | IM2 + 5 g Glucose | |

[a]All media contain $4 \times 10^{-6}$ g/L of biotin.
[b]TM, trace minerals, $CuSO_4.5H_2O$, 60 mg; KI, 80 mg; $MnSO_4.H_2O$, 300 mg; $Na_2MoO_4.2H_2O$, 200 mg; $H_3BO_3$, 20 mg; $ZnSO_4.7H_2O$, 2 g; $FeCl_3.6H_2O$, 4.8 g; $H_2O$ 1L; $H_2SO_4$, 3 mL.

Further Media

All plate media were prepared by adding 15% wt/vol agar to the indicated medium to generate a semi-solid material.

EXAMPLE I

Preparation of Exponentially Growing Yeast 100 mL YM medium were inoculated with a loop full (about $0.5-10 \times 10^6$ cells) of *Pichia pastoris* NRRL Y-12451 and incubated overnight at 30° C. on a gyratory shaker (New Brunswick Scientific, Model G-25). At 8-12 hour intervals, the culture was diluted by a factor of 20-100/1, depending on the turbidity of the culture. Thus, 1-5 mL of the growing culture was diluted to 100 mL with fresh YM medium. The fourth such dilution (carried out at the end of the second day of such transfers) was made so as to obtain an absorbance at 600 nm of about 1.0 after an additional 8-12 hours incubation. The appropriate dilution necessary was determined by trial and error, but generally was about 100/1, though the actual dilution carried out may vary considerably from this value, say 10-500/1.

EXAMPLE II

Mutagenesis

To a 250 mL Erlenmeyer flask was added a 10 mL solution of exponentially growing yeast cells in IM1G media. One mg of nitrosoguanidine (N-methyl-N-nitro-N-nitrosoguanidine) was added to the flask, which was then shaken for 30 minutes on a gyrotary shaker (New Brunswick Scientific, Model G-25) at room temperature (25° C.). This incubation resulted in greater than 98% killing of the yeast cells as determined by viable counts.

The nitrosoguanidine-treated culture was subjected to centrifugation at about $10,000 \times g$ for 10 minutes to separate the yeast cells from the nitrosoguanidine-containing medium. The yeast cells so washed were suspended in 100 mL fresh IM1G medium and incubated at 30° C. for about 10 hours (1-2 generations). The cell density of surviving yeast cells was determined with a Petroff-Hausser counting chamber. Necessary dilutions were made to give 150-200 colonies per plate for subsequent spreading onto plates containing IM1GA or IM1GFT medium. These plates were incubated at 30° C. for 3 days, at which time the viable colonies were retrieved with toothpicks for further purification.

The retrieved isolated single colonies were suspended in 0.5 mL of IM1G medium. The plates were incubated at 30° C. for 2 days. A single colony was picked from the first streak plate, resuspended in 0.5 mL of IM2 medium, and again streaked on plates containing IM2G medium. Material thus purified was subjected to cross-feeding studies as described below.

EXAMPLE III

Cross-Feeding Study

Approximately 1 million cells of *B. subtilis* (trpA) provided by the Bacillus Genetic Stock Center at Ohio State University, Columbus, Ohio, were spread on a plate containing IM2G medium. The viable yeast colonies obtained from the abrine and fluorotryptophan feeding described above were gridded onto the *B. subtilis* inoculated plates. The plates were incubated at 30° C. for 3 days, at which time those colonies surrounded by satellite growth of *B. subtilis* were collected for further testing.

EXAMPLE IV

Tryptophan Determination 100 mL of IM1G or IM1M medium in a 250 mL Erlenmeyer flask was inoculated with yeast cells isolated from the cross-feeding studies, described above. These were maintained at room temperature until all glucose was consumed, as estimated by TES-TAPE® glucose enzymatic test strip, USP (Eli-Lilly), or methanol was consumed, as determined by gas chromatography. The cultures were subjected to direct drying on a freeze-dryer. By direct drying is meant that the entire fermentation mixture was subjected to the freeze-drying procedure.

The dried yeast cells were analyzed for tryptophan content.

Tryptophan contents of the yeast cultures were determined spectroscopically as follows. A stock solution of 21N $H_2SO_4$ containing 0.333 mg/100 mL p-dimethylaminobenzaldehyde was prepared. A 9 mL aliquot of this stock solution was added to 1 mL of water containing about 15–30 mg of yeast cells (microbial cells). The combination was mixed well and stored in the dark overnight (about 18 hours). A fresh solution of 0.05% $NaNO_2$ was prepared just prior to spectroscopic measurements, 3 drops thereof were added to each $H_2SO_4$ solution prepared as described, and the mixture then allowed to stand at room temperature for 30 minutes. The absorbance at 585 nm was measured and plotted for a series of standard solutions, giving a linear curve passing through the origin. Tryptophan content of the various yeast cells samples was determined by reading the results off of the standard curve. The results are presented in Table VIII:

TABLE VIII

| | Tryptophan Content | | | |
|---|---|---|---|---|
| | Glucose Grown | | Methanol Grown | |
| Sample | Wt %[a] | X Control[b] | Wt %[a] | X Control[b] |
| Control (NRRL Y-11430) (Grandparent) | 0.67 | — | 0.63 | — |
| A79 (NRRL Y-15251) | 1.52 | 2.27 | 1.38 | 2.06 |
| A150 (NRRL Y-15252) | 1.88 | 2.81 | 1.30 | 1.94 |
| F5-133 (NRRL Y-15253) | 1.30 | 1.94 | 1.38 | 2.06 |
| F10-76 (NRRL Y-15254) | 1.73 | 2.58 | 1.32 | 1.97 |
| F10-211 (NRRL Y-15255) | 1.45 | 2.16 | 1.43 | 2.13 |
| H-42 (NRRL Y-15256) | 1.61 | 2.40 | 0.83 | 1.32 |

[a]Weight percent amino acid per 100 grams of dried cell weight (weight of dried cells).
[b]Factor by which mutant strain exceeds control in tryptophan content.

Six mutant *Pichia pastoris* yeasts were obtained each exhibiting enhanced tryptophan content compared to the control yeast. The mutant cultures were shown to be both glucose and methanol competent microorganisms.

The yeasts of my invention are seen to provide a protein supplement high in nutritionally available tryptophan.

EXAMPLE V

Most of the mutant isolates described in Example IV were cultured as follows. Isolates growing on YM plates were used to inoculate 100 mL of IM2 medium containing 1 percent by weight glucose in 250 mL Erlenmeyer flasks. Each flask was incubated at 30° C. for four days while being shaken mechanically. Yeast cells from 5 mL of the culture were withdrawn from each flask, subjected to freeze-drying, and then analyzed for tryptophan content as described above. The values obtained are shown in Table IX:

TABLE IX

| Strain | Tryptophan, Wt. % On Glucose |
|---|---|
| Control (NRRL Y-11430) | 0.66, 0.88[a] |
| A79 (NRRL Y-15251) | 1.29 |
| A150 (NRRL Y-15252) | 1.31 |
| F5-133 (NRRL Y-15253) | 1.05 |
| F10-76 (NRRL Y-15254) | 1.06 |
| H-42 (NRRL Y-15256) | 1.42 |

[a]Duplicate analyses.

The results in Table IX show the mutant strains to have significantly higher tryptophan contents than the control strain although they are slightly lower than tryptophan values shown in Table VIII for glucose grown cultures of these same strains using a different growth medium.

EXAMPLE VI

Additional culturing runs were made with the mutant isolates of Example V using 100 mL growth medium IM2 with 0.5 weight percent glucose or 0.5 weight percent methanol as the carbon energy substrate. The cultures were grown in 250 mL Erlenmeyer flasks at 30° C. for three days while undergoing mechanical shaking. A 40 mL sample of each culture was removed, centrifuged, and the cells dried. Tryptophan content of the cells was determined as described above. The results obtained are shown in Table X:

TABLE X

| | Tryptophan, Wt. % | |
|---|---|---|
| Strain | on Glucose | on Methanol |
| Control (NRRL Y-11430) | 0.5 | 0.49 |
| A79 (NRRL Y-15251) | 1.11 | 0.56 |
| A150 (NRRL Y-15252) | 1.24 | 0.56 |
| F5-133 (NRRL Y-15253) | 0.69 | 0.48 |
| F10-76 (NRRL Y-15254) | 0.84 | 0.59 |
| H-42 (NRRL Y-15256) | 1.18 | 0.64 |

In these runs the cultures grown on glucose again show significantly higher tryptophan contents than the control yeast, while the cultures grown on methanol show only slightly higher tryptophan contents except for F5-133 which gave essentially the same tryptophan content as the control.

Fermentation Process For The Production of Single Cell Protein

My invention provides, in several of its aspects, processes for culturing any of the six new strains of microorganisms, mutants thereof which are strains derived from any thereof and also exhibit high tryptophen-producing capabilities, and successive generations of any of these, under aqueous aerobic culturing conditions on suitable carbon energy substrates.

In accordance with my invention, single-cell protein (SCP) products of enhanced tryptophan content are producible by the aerobic aqueous culturing, preferably continuous, of any of the *Pichia pastoris* strains I discovered employing a suitable carbon energy substrate, water, nutrient mineral salts, assimilable nitrogen source, molecular oxygen, and added vitamins particularly such as biotin and/or thiamine as necessary.

Preferred Substrates

The presently preferred substrates for aqueous fermentation conditions of the designated *Pichia pastoris* strains to produce increased tryptophan are the monosaccharides (simple sugars). The data contained hereinabove in Table V, and in my Examples, provides ample guidance to one skilled in the art to select a carbon energy substrate which is suitable and is water-soluble in character.

A variety of substrates can be used. Particular examples include methanol, ethanol, ethylene glycol, propylene glycol, 1-propanol, 2-propanol, glycerol, 1-butanol, and 2-butanol. However, it is apparent that to obtain increased tryptophan response, that such as glucose, dextrose, maltose, dextrin or other partially hydrolyzed starches, and the like, as well as mixtures thereof, should be employed.

Presently preferred is glucose for economy, availability, and enhanced tryptophan content of the cells.

Fermentation Conditions

Fermentation conditions for aerobic fermentation on an oxygenated hydrocarbon feedstock can be employed. Relatively high concentrations of substrates should be avoided. It is generally desirable to maintain the substrate concentration in the ferment at a maximum tolerable level so as to neither starve nor inhibit the growth rates of the microorganism chosen.

Conveniently, the fermentation is conducted in such a manner that the carbon-containing substrate can be controlled as a limiting factor, thereby providing good conversion of the carbon-containing substrate to yeast cells and avoiding potential contamination of the yeast cells with a substantial amount of unconverted substrate.

Continuous operation is preferred for control in production of uniform quantities of uniform products, and most economical uses of all equipment. In a continuous process, the carbon energy substrate, aqueous mineral medium, assimilable nitrogen source, and molecular oxygen-containing gases, are added substantially continuously to the fermentor coupled with continuous withdrawal of aqueous ferment.

If desired, part or all of the carbon energy source material and/or part of the assimilable nitrogen source such as ammonia can be added to the aqueous mineral medium prior to passing the aqueous mineral medium to the fermentor.

Each of the streams introduced into the reactor preferably is controlled at a predetermined rate, or in response to a need determinable by monitoring, such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon energy source, to obtain as high a yield of yeast cells relative to substrate charge as possible.

All equipment, fermentor, piping, and the like, preferably are pre-sterilized. The sterilized reactor is inoculated with a culture of the specified microorganism in the presence of the required nutrients, including molecular oxygen, and the carbon-containing substrate.

The type of fermentor employed is not critical in the practice of the fermentation process of my invention, though presently preferred is operation in a foam-filled fermentor. A fermentor designed to encourage and maintain the produced foam is beneficial to the process of achieving the increased oxygen transfer necessary to maintain desired high cell densities and rapid growth rates.

In starting out a fermentation, the aqueous mineral medium, suitable low initial concentration of carbon energy sorce, assimilable nitrogen source, trace components where desired, and the starting innoculum of *Pichia pastoris* yeast strain are placed in a sterilized fermentor, and suitable flows of oxygen and the various feeds are gradually commenced. It is feasible to begin at low mineral salts levels in the aqueous ferment and build up to a high mineral salts level by feeding an aqueous mineral medium having a high concentration of mineral salts to the ferment, though high salts medium can be added initially to the fermentor to commence immediate operation. One skilled in the art realizes that a brief lag time usually will occur at start-up before the inoculum builds up enough cells for full input of salts and substrate to be utilized.

The fermentation is an aerobic process requiring molecular oxygen which can be supplied by air, oxygen-enriched air, or substantially pure molecular oxygen, to maintain the ferment with an oxygen partial pressure effective to assist the *Pichia pastoris* species in growing in a thriving fashion.

Fermentor designs vary widely in their ability to transfer oxygen to the culture. Although the overall aeration rates can vary over a considerable range, with fermentors that are efficient in oxygen transfer aeration generally is conducted at a rate of about 0.5 to 8, preferably about 1 to 6, volumes (at the pressure employed and at 25° C.) of molecular oxygen-containing gas per liquid volume in the fermentor per minute. This amount is based on air of normal oxygen content being supplied to the reactor, and in terms of pure molecular oxygen the respective ranges would be about 0.1 to 1.7, or preferably about 0.2 to 1.3, volumes (at the pressure employed and at 25° C.) of molecular oxygen per liquid volume in the fermentor per minute.

The pressure employed for the microbial fermentation step can range widely. Typical pressures are about 0 to 150 psig, presently preferably about 0 to 60 psig, more preferably at least slightly over atmospheric pressure, as a balance of equipment and operating costs versus oxygen solubility is achieved. Greater than atmospheric pressures tend to increase the dissolved oxygen concentration in the aqueous ferment, which in turn can help increase cellular growth rates.

Fermentation temperatures can vary somewhat, generally as in the range of about 25° C. to 65° C., though preferably for these strains should be close to about 30° C.

Assimilable nitrogen can be supplied by any nitrogen-containing compound or compounds capable of releasing nitrogen in a form suitable for metabolic utilization by the yeast microorganism. While a variety of organic nitrogen source compounds, such as protein hydrolysates, technically can be employed, particularly in small batch fermentations usually cheaper nitrogen-containing compounds such as ammonia are utilized in practice. Ammonia gas is convenient for large scale operations, and also assists in pH control.

The pH range in the aqueous microbial ferment should be in the range of about 3 to 7, preferably about 3.5 to 5.5. Preferences of certain microorganisms for a pH range are dependent to some extent on the medium employed, as well as on the particular microorganism, and thus may change somewhat with change in medium as can be readily determined by those skilled in the art.

The average retention time of the aqueous ferment in the fermentor can vary considerably, depending in part on the fermentation temperature and yeast culture employed. Generally, the retention time will be about 2 to 30 hours, preferably presently about 4 to 14 hours, based on average retention.

Preferred High Cell Density Fermentation

Although the composition of the aqueous ferment can vary considerably, depending in part on the yeast and substrate employed, the minerals content in the ferment (that is, liquid plus cells) for maximum efficiencies is maintained at relatively high levels. Set forth in the Table below are the minimum, broad, and presently preferred ranges of concentrations of various elements in the ferment for high salts operation, the concentration being expressed as of the element, though it is recognized that all or part of each can be present in the form of a soluble ion, or in cases such as P are present in a combined form of some type such as phosphate. The amount of each element is expressed in grams or milligrams per liter of ferment (aqueous phase, including cells):

| | Weight of Element per Liter of Ferment | | |
|---|---|---|---|
| Element | Minimum | Broad Range | Preferred Range |
| P | 1.9 g | 1.9–20 g | 2.2–10 g |
| K | 1 g | 1–20 g | 1.5–10 g |
| Mg | 0.15 g | 0.15–3 g | 0.3–1.2 g |
| Ca | 0.06 g | 0.06–1.6 g | 0.08–0.8 g |
| S | 0.1 g | 0.1–8 g | 0.2–5 g |
| Fe | 6 mg | 6–140 mg | 9–80 mg |
| Zn | 2 mg | 2–100 mg | 3–40 mg |
| Cu | 0.6 mg | 0.6–16 mg | 1–10 mg |
| Mn | 0.6 mg | 0.6–20 mg | 0.9–8 mg |

Some of the metals required are advantageously added in the form of a sulfate, so that the minimum concentrations of sulfur normally are exceeded. Preferably, the magnesium, calcium, iron, zinc, copper, and manganese are employed in the form of a sulfate or chloride. The potassium preferably is employed as a sulfate, chloride, or phosphate. The phosphorus preferably is employed in the form of a phosphate.

Other elements which may be present, at least in trace amounts, include such as sodium and cobalt, e.g., as a halide or sulfate, molybdenum, e.g., as molybdate; boron, e.g., as borate; selenium, e.g., as selenite or selenate; or iodine, e.g., as iodide.

In typical high cell density fermentation, the ferment will comprise about one-half supernatant medium and one-half cells, by volume. These one-half by volume cells, however, will contain at least about two-thirds of the mineral salts content of the aqueous ferment.

The salts in the supernatant are at a relatively low concentration, since there is a high take-up by the growing reproducing cells. The mineral salts in the cells may not be as fed or applied since some may be a bound organic form. Mineral analysis of the ferment, of course, would reflect a total mineral content.

In addition to the mineral salts, vitamins (organic growth factors) can be employed in the ferment as is known in the art, when their presence is desirable for the propagation of the particular yeast chosen.

Product Recovery

The yeast cells produced process can be recovered in any convenient manner. If desired, extracellular products can be recovered from the substantially cell-free remaining supernatant liquid by conventional means. The substantially cell-free effluent can be treated, for example, with acetone or a lower alcohol such as methanol or ethanol to precipitate any polymeric material produced extra-cellularly. The cell-free effluent also can be treated by solvent extraction and/or base extraction to recover, if desired, other extra-cellular products such as pigments, vitamins, or organic acids produced during the culturing process. The cell-free effluent, with or without such intervening treatment, can be returned to the fermenter as a part of the aqueous makeup, or as a substantial or almost total part of the aqueous makeup, to avoid waste disposal problems insofar as possible.

The microbial cells usually are killed by heat or chemical means, and this can be done before or after the separation of the cells from the fermenter effluent. The yeast cells are a valuable source of protein for man as well as beast. For human consumption, the cells can be treated as necessary to reduce the nucleic acid, but for animal feed purposes such treatment does not appear presently necessary.

In a process employing the preferred high salts mode of operation, a cell density of about 60 to 160 grams of yeast cells, on a dried basis, per liter of fermentation admixture, can be obtained in high yield. If desired, the cells can be recovered from the fermentation admixture by centrifugation or other separation means. If desired, the concentrated cells then can be washed such as by mixing with water, and separated such as by recentrifuging, or by adding water prior to or during centrifugation to substantially free the cells of mineral medium, and the washings including the separated mineral medium then can be returned to the fermenter as water and mineral medium makeup, thus substantially reducing or avoiding waste disposal problems. The recovered cells then can be simply dried to produce a dried product for future use. If desired, the high cell density fermenter effluent in total can be dried to produce a whole dried product of dried cells and residual water soluble substances including salts, and this whole-dried product used as a very useful animal feed of high protein-high salts character.

The disclosure, including data, illustrates the value and effectiveness of my invention. The examples, the knowledge and background of the field of the invention, general principles of microbiology, chemistry, and other applicable sciences, have formed the bases from which the broad descriptions of my invention, including the ranges of conditions and generic groups of operant components, have been developed, and which have formed the bases for my claims here appended.

I claim:

1. A biologically pure culture of yeast having the identifying characteristics of a *Pichia pastoris* and exhibiting tryptophan producing capability when cultured on a substrate selected from the group consisting of methanol and glucose, wherein said yeast is selected from the group consisting of:
   *Pichia pastoris* A79 (NRRL Y-15251),
   *Pichia pastoris* A150 (NRRL Y-15252),
   *Pichia pastoris* F5-133 (NRRL Y-15253),
   *Pichia pastoris* F10-76 (NRRL Y-15254),
   *Pichia pastoris* F10-211 (NRRL Y-15255), and
   *Pichia pastoris* H-42 (NRRL Y-15256).

2. A biologically pure culture according to claim 1 wherein said yeast is *Pichia pastoris* A79 (NRRL Y-15251).

3. A biologically pure culture according to claim 1 wherein said yeast is *Pichia pastoris* A150 (NRRL Y-15252).

4. A biologically pure culture according to claim 1 wherein said yeast is *Pichia pastoris* F5-133 (NRRL Y-15253).

5. A biologically pure culture according to claim 1 wherein said yeast is *Pichia pastoris* F10-76 (NRRL Y-15254).

6. A biologically pure culture according to claim 1 wherein said yeast is *Pichia pastoris* F10-211 (NRRL Y-15255).

7. A biologically pure culture according to claim 1 wherein said yeast is *Pichia pastoris* H-42 (NRRL Y-15256).

* * * * *